United States Patent [19]

Koerbacher

[11] 4,050,466
[45] Sept. 27, 1977

[54] ENDOTRACHEAL TUBE

[76] Inventor: Kathleen C. Koerbacher, 636 Bonneau Lane, Mount Pleasant, S.C. 29464

[21] Appl. No.: 620,562
[22] Filed: Oct. 8, 1975
[51] Int. Cl.² .......................................... A61M 25/00
[52] U.S. Cl. ................................. 128/351; 128/208
[58] Field of Search .................. 128/348, 351, 208

[56] References Cited
U.S. PATENT DOCUMENTS

| 2,912,982 | 11/1959 | Barsky | 128/351 |
| 3,388,705 | 6/1968 | Grosshandler | 128/351 |
| 3,599,642 | 8/1971 | Tindel | 128/351 |
| 3,848,605 | 11/1974 | Harautuneian et al. | 128/351 |
| 3,964,488 | 6/1976 | Ring et al. | 128/351 |

Primary Examiner—Dalton L. Truluck
Attorney, Agent, or Firm—Wellington M. Manning, Jr.; Luke J. Wilburn, Jr.

[57] ABSTRACT

An endotracheal tube of one-piece plastic construction having a distal tubular portion for insertion within a patient's mouth into the trachea connected by a flexible, accordion section to a proximal tubular portion arranged for connection to associated medical apparatus. The proximal end of the tube is disposed in overlying relationship with the patient's chin to remove medical apparatus from any sight or physical interference at the patient's face area.

7 Claims, 3 Drawing Figures

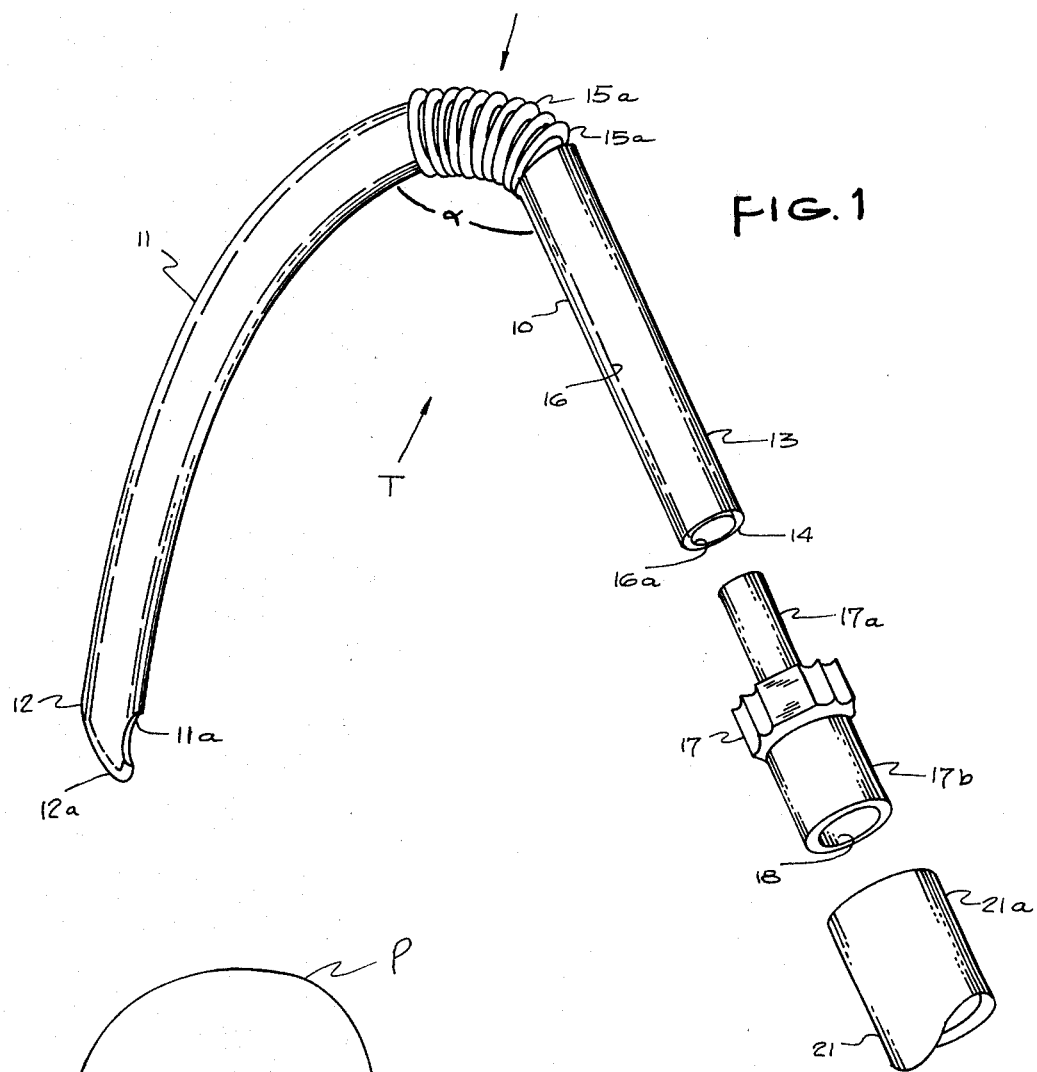
FIG. 1
FIG. 2
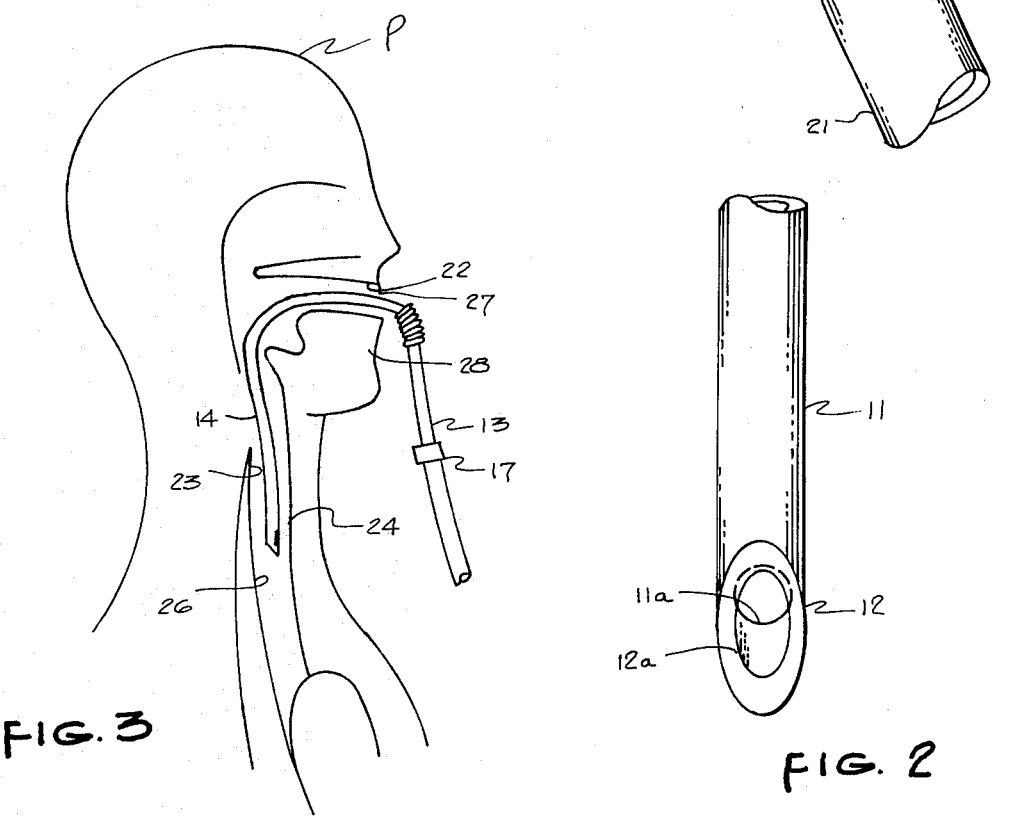
FIG. 3

ENDOTRACHEAL TUBE

BACKGROUND OF THE INVENTION

A commonly used device in the medical field is an endotracheal tube which is particularly useful during surgical procedures for maintaining control over the patient's breathing. Commonly, endotracheal tubes are manufactured from resilient type materials and are used to control ingress and egress from the patient's trachea. The endotracheal tube insures an unobstructed passageway during surgery and permits controlled respiration of the patient. Also quite importantly, the endotracheal tube prevents blood, mucus, vomitus, and irrigating solutions from entering the respiratory tract and may be used to remove mucus and any other solution from the respiratory tract.

As is well known, present day endotracheal tubes are inserted through the patient's mouth and beyond, into the vestibular portion of the trachea. The outer end of the tube is connected to suitable medical apparatus such as a suction device for aspirating the trachea, a source of anesthesia or the like. In a typical arrangement, the outer end of present day endotracheal tubes are arranged to be connected to the associated medical apparatus by a suitable fitting or other means so that the outer portion of the tube and attendant connectors, hoses, etc., are disposed in front of the patient's face during use of the tube. Surgical procedures, such as plastic surgery on the face, lips, etc., are difficult with these various component parts providing a source of interference to the surgeon. The surgeon's view and manipulations are obstructed along with the view of the anesthesiologist. The obstruction problem is aggravated in the particular case of infants and small children whose facial area is rather small in comparison to the endotracheal tube.

It can further be understood that once the endotracheal tube and attendant apparatus have been properly positioned with respect to the patient awaiting surgery, the stage is set. Any movement of the apparatus during the surgical procedure may cause a misalignment of the tube within the patient's trachea which could lead to malfunction of same.

The present invention provides an endotracheal tube which overcomes the abovenoted disadvantages of prior art tubes. Moreover, no prior art is known that would teach or suggest the tube of the present invention.

SUMMARY OF THE INVENTION

A primary object of the present invention is to provide a new and novel endotracheal tube.

Another object of the present invention is to provide a new and novel endotracheal tube which avoids any interference with a surgeon during use of the tube in surgery.

A further object of the present invention is to provide a new and novel endotracheal tube which is simple and inexpensive in construction, which may be easily manufactured in any size within a wide range, and which may be disposed after a single use.

The present invention generally relates to an endotracheal tube comprising a tubular body having a distal end and a proximal end, said distal and proximal ends being connected by said tubular body, said body having a bend therealong whereby said distal and said proximal ends have an angle of at least 90° therebetween, said proximal end being adapted for connection to associated medical apparatus by way of a coupling means, said distal end of said tube being receivable in a patient's trachea, whereby said coupling means on said proximal end of said tube is located away from the patient's face and generally provides no obstruction to surgical procedures.

The present invention further contemplates the provision of a new and novel endotracheal tube which may be sized for use on either infants or adults, and which may permit easy positioned insertion and positioning on the patient while being easily maintained in a proper position during the surgical procedures. The present tube may also be simply and easily attached to associated medical apparatus in the operative position.

The tube of the present invention is preferably of unitary construction of a resilient material such as rubber or polyvinyl chloride. Moreover, the coupling section between the distal and proximal ends of the tube preferably has an accordion pleated section therealong. The accordion pleats permits maintenance of the desired angular relationship of the two ends. A preferred range of angles is in the range of 90° to 105° with an angle of approximately 105° being most preferred. The proper angular relationship enables the endotracheal tube to be employed on small children while removing any possible visual or physical obstructions to the surgeon.

BRIEF DESCRIPTION OF THE DRAWINGS

FIG. 1 is a perspective view of an endotracheal tube constructed in accordance with the present invention.

FIG. 2 is an enlarged view of the distal end of an endotracheal tube according to the teachings of the present invention.

FIG. 3 is a schematic cutaway view of a tube according to the present invention inserted into the trachea of a patient.

DESCRIPTION OF THE PREFERRED EMBODIMENTS

Referring now to the drawings and to FIG. 1 in particular, there is shown an endotracheal tube, generally designated by the letter T, and constructed in accordance with the present invention. In the illustrated embodiment, endotracheal tube T is preferably fabricated as a unitary or one-piece constructed article. Synthetic resinous materials such as polyethylene, polypropylene and the like are preferred materials of construction from which the tube can be manufactured.

Endotracheal tube T comprises a tubular body member 10 which includes a tubular rear portion 11, preferably of arcuate shape as shown, having a distal end 12, and a tubular front portion 13 having a proximal end 14. Front tubular portion 13 is preferably substantially straight in configuration. The tubular body member 10 of tube T also includes a tubular connecting portion 15 disposed intermediate rear tubular portion 11 and front tubular portion 13. Connecting portion 15 is preferably of flexible construction to permit free pivotal, relative movement of front and rear portions 11 and 13 respectively.

In the preferred embodiment, the connection portion 15 is formed of a plurality of annular, accordion-like pleats 15a. Thus, the front portion 13, connecting portion 15 and rear portion 11 of the body member 10 are integral and are provided with a central bore 16 extending continuously from the distal end 12 to the proximal end 14.

Tubular connecting portion 15 may also be of rigid or semi rigid construction though the flexible portion is preferred. Also the angle α (FIG. 1) between front tubular portion 13 and rear tubular portion 11 should be at least 90° and preferably approximately 105°. A general range of 90° to 110° is acceptable for angle α.

Distal end 12 of tubular rear portion 11 is preferably angularly disposed in a plane extending obliquely to the axis of the rear portion so as to facilitate insertion of the rear portion 11 into the mouth and larynx of the patient.

As particularly illustrated in FIG. 2, distal end 12 of tube 10 is beveled at 12a. A beveled top 12a of distal end 12 permits easy insertion of tube 10 into the trachea of a patient without causing undue irritation or possible damage to the patient. Also as shown in FIGS. 1 and 2, distal end 12 has an opening 11a through side wall 11 which facilitates better results with the tube 10 in performance of its normal functions.

Central bore 16 of endotracheal tube 10 terminates at proximal end 14 with an opening 16a which is of a particular diameter for connection to the desired medical apparatus. A tube coupling 17 is provided having a male end 17a and a female end 17b. Coupling 17 further has a base 18 extending completely therethrough. As illustrated in FIG. 1, coupling 17 has a single female end 17b, and a single male end 17b, of the standard, and customary outside diameter of 22 mm. necessary to cnnect tube 10 to the anesthetic source. Male and female connection could be reversed if desired.

Coupling 17 may thus be attached to tube 10 by inserting male end 17a into opening 16a of base 16. Likewise, an end 21a of a conduit 21 may be received within female end 17b of coupling 17 to tie tube 10 into the desired apparatus. Conduit 21 may thus be in line with the associated apparatus to introduce materials into or aspirate materials from the patient's trachea, through the tube 10 of the present invention.

Having particularly described the endotracheal tube T of the present invention, the procedure for use of same will now be described, making reference to FIG. 3. Tube 10 is inserted through the mouth 22 and larynx 23 of a patient P. Coupling 17 is attached to conduit 21 while tube 10 is received on male member 17a. The distal end 12 of tube 10 will be properly positioned in the vestibular portion 24 of the trachea 26 by manipulation of front tubular portion 13. The patient is, of course, anesthetized and does not feel any pain or discomfort during placement of tube 10.

Once tube 10 is properly positioned, connecting portion 15 resides adjacent the patient's lips 27. Front portion 13, coupling section 17 and conduit 21 of tube 10 are then located below lips 27 due to flexibility of connecting portion 15 or the angle α produced between front and rear portions 13 and 11 respectively. Tube T can thus be secured in place by use of strips of surgical tape (not shown). This particular arrangement removes all major obstructions from the view of the surgeon and the surgical procedure can proceed with more efficiency and dispatch. Also, if necessary, front portion 13 of tube T may be manipulated somewhat without any appreciable movement of distal end 12 on the trachea due to the flexibility of coupling tubular portion 15.

Having described the present invention in detail, it is obvious that one skilled in the art will be able to make variations and modifications thereto without departing from the scope of the invention. Accordingly, the scope of the present invention should be determined only by the claims appended hereto.

What is claimed is:

1. An endotracheal tube comprising a unitary tubular body member, said body member having an elongated arcuately shaped rear portion for insertion into the trachea, said rear portion having a beveled distal end, with side wall opening therein said body member further having an accordion pleated mid portion and a substantially straight, elongated front portion, said mid portion being yieldable to define an angle between said rear and front portions of at least about 90° to about 110°, and said front section being adaptable to receive a coupling member at a proximal end and being sufficient in length to place said coupling at a point away from a patient's mouth to avoid physical or visual impairment during use.

2. An endotracheal tube as defined in claim 1 wherein the body member is formed from a synthetic resinous material.

3. An endotracheal tube as defined in claim 2 wherein said rear portion of said body member has an opening through the side wall adjacent the distal end.

4. An endotracheal tube in accordance with claim 1 wherein said distal end on said tubular rear portion is angularly disposed in a plane extending obliquely to the axis of said rear portion.

5. An andotracheal tube in accordance with claim 4 wherein said tubular front portion is provided with a central bore of a selected diameter, said bore diameter being selected to accommodate an adapter on said associated medical apparatus.

6. An endotracheal tube as defined in claim 1 wherein said angle between said front and rear portions is approximately 105°.

7. An endotracheal tube comprising a unitary tubular body member made from synthetic resinous material, said body member having an elongated arcuately shaped rear portion for insertion into the trachea, said rear portion having a beveled distal end and having an opening in the tube side wall adjacent said distal end, said body member further having a mid portion joining said rear portion and made up of a plurality of accordion-like pleats, and an elongated, substantially straight front portion, said mid portion being sufficiently yieldable to define an angle of at least about 90° to about 110° between said front and rear body portions, said front section further being adapted at a proximal end to receive a coupling thereat, and being sufficient in length to permit securement of said tube thereat to the body of a patient and to position a coupling connectable thereto sufficiently removed from a patient's mouth to avoid any physical or visual impairment during use.

* * * * *